United States Patent [19]

Zachariades

[11] Patent Number: 4,655,769

[45] Date of Patent: Apr. 7, 1987

[54] ULTRA-HIGH-MOLECULAR-WEIGHT POLYETHYLENE PRODUCTS INCLUDING VASCULAR PROSTHESIS DEVICES AND METHODS RELATING THERETO AND EMPLOYING PSEUDO-GEL STATES

[76] Inventor: Anagnostis E. Zachariades, 65 Glengarry Way, Hillsborough, Calif. 94010

[21] Appl. No.: 811,015

[22] Filed: Dec. 18, 1985

Related U.S. Application Data

[63] Continuation-in-part of Ser. No. 664,244, Oct. 24, 1984, abandoned.

[51] Int. Cl.⁴ .................. A61F 2/06; C08J 9/28; B29C 43/00; B29C 55/22
[52] U.S. Cl. .................. 623/1; 138/103; 138/129; 264/41; 264/288.8; 264/299; 264/331.15; 521/64; 521/143; 623/16
[58] Field of Search .......... 264/41, 49, 288.8, 299, 264/331.15; 521/79, 143, 64; 623/1; 138/103, 129

[56] References Cited

U.S. PATENT DOCUMENTS 3,954,927 5/1976 Duling et al. .................. 264/49
4,413,110 11/1983 Kavesh et al. .................. 526/348.1
4,440,211 4/1984 Kwon et al. .................. 264/185

OTHER PUBLICATIONS

Lemstra, Piet J. and Paul Smith "Ultra-Drawing of High Molecular Weight Polyethylene" In *British Polymer Journal*, Dec. 1980, pp. 212–214.

Primary Examiner—Philip Anderson
Attorney, Agent, or Firm—Owen, Wickersham & Erickson

[57] ABSTRACT

A pseudo-gel comprising a suitable solvent in an amount of 99 to 90 percent by weight and an ultra-high-molecular-weight polyethylene in an amount of 1 to 10 percent by weight, said polyethylene being a semicrystalline network with adjustable crystalline morphology comprising randomly dispersed and oriented chain-folded single crystals, stacks of single crystals, spherulite crystals, and extended-chain shish-kebab-type of fibrils with lengths up to a few millimeters and widths up to 20 μm. Also, the semicrystalline ultra-high molecular-weight polyethylene obtained by removal of said solvent from the pseudo-gel. Further, a method for making the pseudo-gel and the ultra-high-molecular-weight polyethylene product.

37 Claims, 15 Drawing Figures

ULTRA-HIGH-MOLECULAR-WEIGHT POLYETHYLENE PRODUCTS INCLUDING VASCULAR PROSTHESIS DEVICES AND METHODS RELATING THERETO AND EMPLOYING PSEUDO-GEL STATES

REFERENCE TO RELATED APPLICATION

This application is a continuation-in-part of application Ser. No. 664,244, filed Oct. 24, 1984 now abandoned.

This invention relates to a novel ultra-high-molecular-weight polyethylene product, useful for vascular prosthesis devices and for both industrial and biomedical uses calling for high-impact, low-friction, high wear-resistance, high-porosity, and softness or for one or more of these qualities. The invention also relates to such devices. It further relates to a novel method for processing solution-grown ultra-high molecular weight polyethylene crystalline morphologies which may form pseudo-gel states when the polymer is dissolved in a suitable volatile or non-volatile solvent at an elevated temperature and the solution is cooled to or below the temperature at which the polymer crystals are grown. Additionally it relates to methods involving further processing of the pseudo-gel states and their products after solvent extraction into profiles and shapes with physical and mechanical properties that may be tailored to specific biomedical (e.g., vascular and orthopedic prosthesis and sutures) and industrial applications.

BACKGROUND OF THE INVENTION

Qualities such as softness, porosity, and biocompatibility have long been sought in the field of vascular prosthesis.

The development of vascular prostheses has been a subject of extensive work over the last 25 years. Most synthetic vascular prostheses have been products of the application of textile technology in this field and have been woven or knitted tubular structures designed to resemble the softness and flexibility of the natural blood vessels. The two major synthetic polymers used as vascular prostheses have been Dacron polyester and polytetrafluoroethylene (PTFE).

These woven or knitted tubular structures are porous and have been produced with smooth or velour surfaces. The porosity, which has been claimed to play a determinant role for the healing process of the arterial prostheses, can be controlled to some extent by adjusting the thread size, or the interstices size, and by the texturization or knit pattern of the synthetic fabric. High degrees of porosity may lead to excessive blood loss after implantation; the velour has been claimed to have the advantage that it fills the interstices of the underlying fabric, thus reducing implant bleeding without reducing the porosity of the implant.

The DeBakey Ultra-light-weight Knitted Prosthesis (USCI, Inc.), the Cooley Graft and the Wesolowski Weavenit (Meadox, Inc.) and the Microknit (Golaski Lab, Inc.) are "smooth wall" commercial Dacron arterial prostheses of different geometric and compositional configurations; the Sauvage Filamentous Velour Prosthesis (USCI, Inc.) is an example of a velour Dacron vascular prosthesis material.

Woven PTFE prostheses have low porosity and have not been used as much as the Dacron prostheses. Also, it has been suggested that their use should be temporary, their permanent use being "dangerous". More recently, "expanded" PTFE, called "Gore-tex" (W. L. Gore & Assoc., Inc.) has become available. "Gore-tex" is a network of small nodules interconnected by thin fibrils and with an adjustable porosity from 0 to 96%, and it has been used with generally encouraging results. Studies with smooth vascular prostheses of expanded PTFE (85% porosity) and with ultra-light weight woven PTFE showed that the patency (i.e., openness or non-occlusion) of the expanded PTFE prostheses was significantly longer (4.5–10 months) in comparison to the woven PTFE prostheses, which occluded in 101 days. It was also demonstrated that the porosity played a critical role in the healing process.

A recent theoretical calculation of the porosity in woven fabrics shows that although their porosity can be designed to vary over a wide range, the existing woven vascular prostheses, e.g. Woven Cooley and Woven DeBakey prostheses have had a low degree of porosity which might not permit complete healing, particularly in small diameter, low-blood-flow locations where the 5 year patency rate is less than 30%.

Ultra-high-molecular-weight polyethylene (UHMWPE) is another polymer which has attracted the interest of many workers for the preparation of artificial prostheses, particularly the construction of orthopedic joint devices, because of its outstanding abrasion resistance and strength. UHMWPE, in contrast to the conventional high-density polyethylenes having average molecular weights up to approximately 400,000, has an extremely high molecular weight, typically 2–8 million, and is intractable. The polymer is supplied as fine powder and is processed into various profiles using compression molding and ram extrusion processes. The intractability of the polymer can be overcome by varying the degree of material cohesion and its initial morphology, more specifically by the formation of gel states and single-crystal mat morphologies and by heating the polymer melt to high temperature ranges, under inert conditions, in which the viscosity of the melt is reduced significantly for melt processing. The preparation of UHMWPE gel states and single crystal mat morphologies have been pursued predominantly for the development of ultra-high modulus and strength fibers. Melt processing of UHMWPE at high temperatures under inert conditions has been investigated for the development of melt-crystallized morphologies with enhanced mechanical properties which may result from the material cohesion which is achieved by processing under such conditions.

Although the prior art covers to a large extent the preparation of superstrong UHMWPE fibrous morphologies by spinning processes which involve a gel intermediate, the focus of the works has been mainly on the development of filamentary products with high modulus and strength in one direction. Also, there has been an expressed desire that such filamentary products have reduced porosity, because porosity may have an adverse effect on the effective transmission of load within the oriented filamentary products. On the contrary, the development of products with bulk properties or enhanced isotropic mechanical properties from gel-like precursors has received no attention. Furthermore, little effort has been devoted to determining the effect of the morphology of the gel-like precursor on the physical properties and the deformability of the products from gel-like precursors. These areas fall within the scope of my invention and they have a potential impact on the production of biomedical devices such as vascular and orthopedic prostheses and sutures and also on the fabrication of profiles possessing the outstanding wear properties of UHMWPE.

An example of a stretched UHMWPE fiber and a process for making it is U.S. Pat. No. 4,413,110. There a slurry of polymer in paraffin oil is heated to between 180° and 250° C., preferably 200°–240° C. and is then cooled to a temperature between −40° C. and +40° C., the paraffin oil being replaced by a more volatile solvent at a temperature below 50° C. and the cooling being rapid and done in such a way as to produce a "gel fiber". This "gel fiber" is then treated to evaporate the more volatile solvent and to stretch the "xerogel" fiber, as it is called, at 120° C. to 160° C., preferably above 135° C. The porosity of the resultant fiber is stated to be "no more than about 10% (preferably no more than about 6% and more preferably no more than about 3%)".

SUMMARY OF THE INVENTION

The present invention includes the formation and use of UHMWPE pseudo-gels.

The term gel in the prior art referred to a macroscopically coherent structure, that (1) is spatially cross-linked, (2) comprises a major amount of low molecular-weight liquid, and (3) exhibits elastic properties not unlike those of solids.

On the contrary, in this specification and in the claims the terms "pseudo-gel" and "gel-like" refer to a concentrated solution of organic polymer which contains an entangled three-dimensional semicrystalline network the morphology of which may vary with the conditions of preparation or crystallization, for example, when the pseudo-gel of this invention is prepared under isothermal and quiescent conditions, the crystals in the pseudo-gel have predominantly a lamellar morphology, with single crystals or spherulitic crystals. The number of single crystals decreases, and the crystalline morphology becomes more complex as the solution concentration increases. On the other hand, when the pseudo-gel of this invention is prepared under non-isothermal and quiescent conditions, a large fraction of extended chain crystals (shish-kebab crystals) are also present. However, because the molecular entanglements in this semicrystalline network are not permanent, such solutions undergo flow when a shear stress, no matter how small, is applied. Therefore, such pseudo-gels exhibit time-dependent elastic properties and are not true gels, as the term is properly used, because they do not possess an equilibrium shear modulus.

In contrast to the prior art, the present invention provides for the preparation of an UHMWPE crystalline morphology with isotropic mechanical properties from a pseudo-gel precursor. Different crystalline morphologies are obtainable under different processing conditions. This crystalline morphology has an enhanced porosity which cannot be exhibited by melt-crystallized morphologies, and it is readily deformable in the solid state into products with different properties in one or more directions.

This invention provides a method for the preparation of UHMWPE vascular prostheses by processing the UHMWPE in the pseudo-gel state. The pseudo-gel is prepared by dissolving a suitable concentration of the polymer in a suitable solvent, preferably a non-volatile solvent, at an elevated temperature well above the temperature at which the pseudo-gel forms and then cooling to or below the temperature at which the polymer crystals grow and the pseudo-gel forms. The pseudo-gel is subsequently processed under compression or tension into products of different profiles. Extraction of the solvent from the shaped pseudo-gel products leads to semicrystalline porous morphologies with geometrical configurations analogous to those of their pseudo-gel precursors. These morphologies may be processed further, at a temperature below or close to their melting point.

This invention provides also a method for the construction of vascular prostheses by (a) compressing the pseudo-gels into thin films between hot plates, e.g., at 100°–170° C., (b) wrapping the pseudo-gel film around a rotating mandrel into a multilayer tubular structure, and (c) extracting the non-volatile solvent from the tubular structure on the mandrel, for example extracting first with a more volatile solvent and then drying out the tubular structure by evaporating the more volatile solvent.

This invention also provides for the preparation of anisotropic UHMWPE morphologies with enhanced mechanical properties, obtained by solid-state deforming, i.e., at a temperature near or below the melting point of UHMWPE, the semicrystalline polymer after extraction of the solvent, by extrusion, drawing, molding, and forging techniques.

This invention also provides for the preparation of an UHMWPE semicrystalline material which has adjustable porosity from zero up to more than 90%. This material can be made with sufficient body to maintain its shape and cross-sectional area; it is uniformly expensive and readily deformable to generate products with bulk properties, in contrast to filamentary products.

SOME DIFFERENCES IN BEHAVIOR BETWEEN TRUE GELS AND THE PSEUDO-GELS OF THIS INVENTION

The contrast between true gels and a pseudo-gel is shown in FIGS. 12-15.

Figure 12:
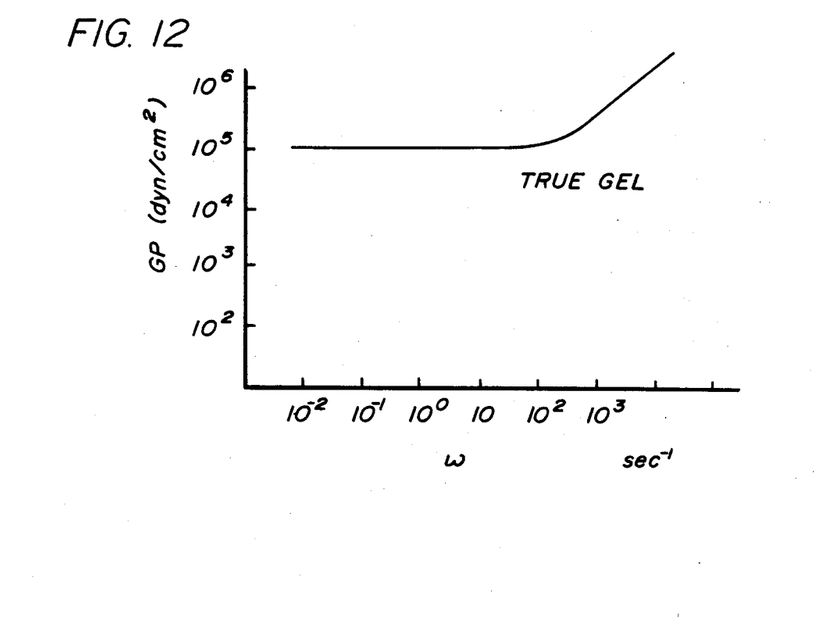
FIG. 12 is a graph showing a plot of the shear modulus of a true gel in dynes per square centimeter against frequencies from 1/100 to 1000 per second.
Figure 13:
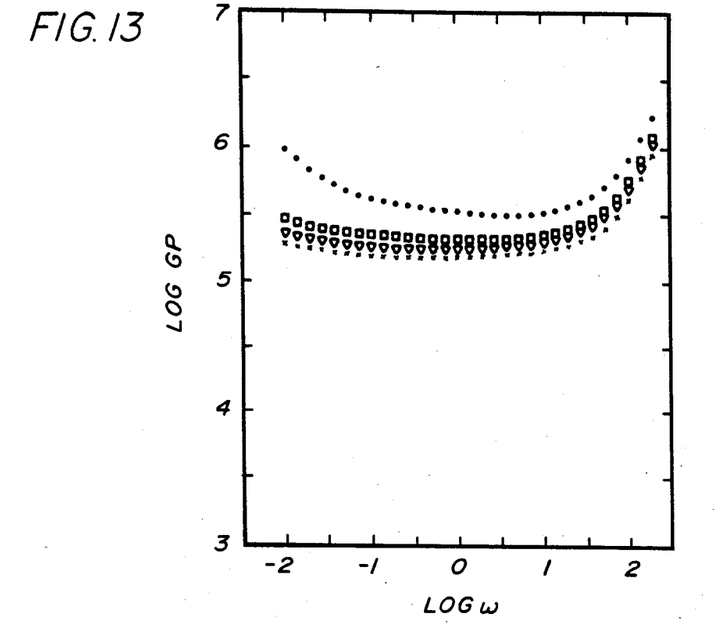
FIG. 13 is a graph of the behavior of a pseudo-gel of this invention on four successive frequency sweeps, with shear modulus (log GP) plotted against the logarithm of the frequency $\omega$.

FIG. 12 shows that for a true gel, the shear modulus, up to a point, is independent of the frequency. In contrast, FIG. 13 shows that the pseudo-gel of ultra high molecular weight polyethylene (UHMWPE) in paraffin oil is shear sensitive; (a) the shear modulus is dependent on frequency, (b) the shear modulus is dependent on shear history; after one or more shearing cycles there is always a different shear modulus at any particular frequency. Here there were four cycles reading them from the top down, on a 4% UHMWPE gel-like system in paraffin oil at 25° C.

Figure 14:
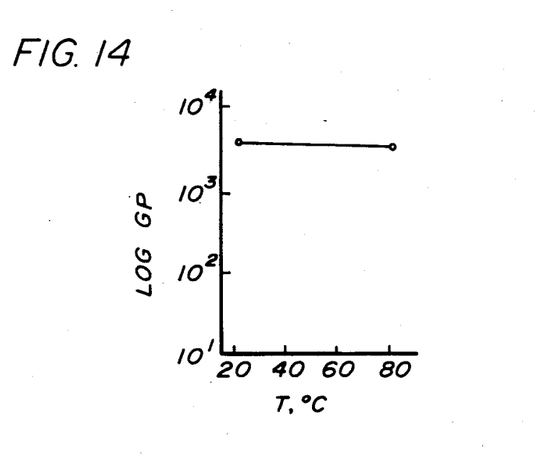
FIG. 14 is a graph showing the response of a true gel to temperature, plotting shear modulus (as log GP, in Newtons per square meter) versus temperature T in degrees centigrade.
Figure 15:
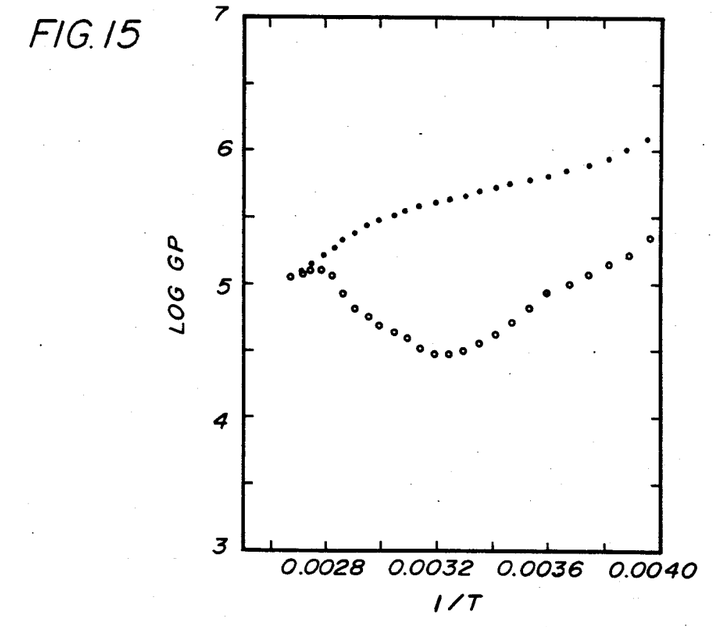
FIG. 15 is a graph showing the response of a pseudo-gel of this invention to temperature, plotting the shear modulus (log GP) against the reciprocal of the temperature T; during a heating and cooling cycle at a frequency $\omega = 100$ per second.

FIG. 14 shows that the shear modulus of a true gel is independent of temperature, at least within a range, while FIG. 15 shows the hysteresis behavior of a 3% UHMWPE pseudo-gel of this invention during a heating (solid dots) and cooling cycle (hollow dots) at frequency $\omega = 100$ per second. The shear modulus is dependent on temperature, decreasing significantly with temperature. Also, during a thermal cycle, heating then cooling, the initial shear modulus cannot be reached again.

DESCRIPTION OF SOME PREFERRED EMBODIMENTS OF THE INVENTION

Figure 1:
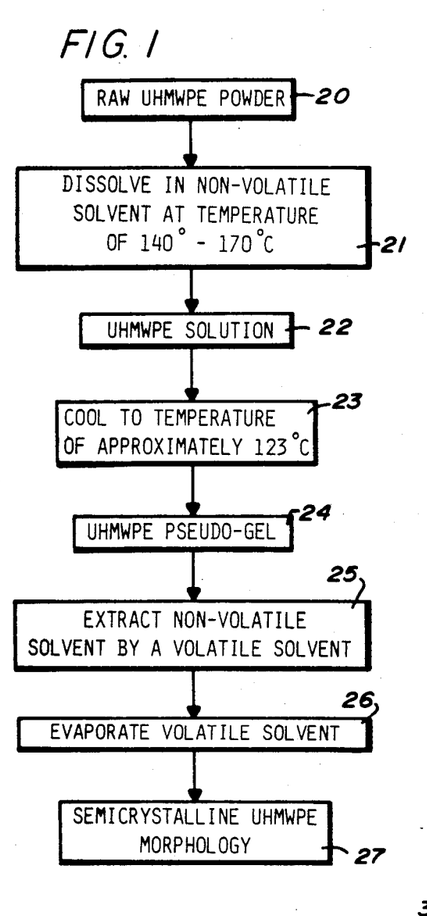
FIG. 1 is a flow sheet of a process embodying the principles of the invention.

As shown in FIG. 1, an UHMWPE pseudo-gel according to this invention may be prepared from a raw UHMWPE powder 20 by dissolving the UHMWPE in a solvent at 21, preferably a non-volatile solvent such as paraffin oil, in a temperature range from 140°-170° C., preferably in the high end of the temperature range in order to disrupt the thermally persistent extended chain morphology of the raw UHMWPE powder and decrease the number of nucleation sites which allow for the preparation, upon cooling, of large lamellar single crystals. These are known to have a more regular chain folded crystalline morphology than melt-crystallized and solution-grown crystal morphologies obtained by rapid cooling, and therefore have fewer intercrystalline and intracrystalline tie molecules. Such tie molecules affect the deformation behavior of the semicrystalline morphologies that are obtained after extraction of the solvent from the pseudo-gel.

An UHMWPE used in this work was a HiFax 1900 (Hercules, Inc.) with an average molecular weight of $2-8 \times 10^6$. The UHMWPE was added slowly to the paraffin oil (MCB Reagents, EM Science, PX 0045-3) to concentrations from 1 to 8% by weight. To avoid degradation of the polymer at high temperatures, the polymer is preferably stabilized with approximately 0.5 wt. % (based on the polymer) of BHT antioxidant (butyl hydroxy toluene) and heated under inert conditions, e.g., in nitrogen gas. The mixtures are stirred slowly, at 60 to 600 r.p.m., under constant conditions at a temperature of 150° C. Under these conditions, a clear solution was obtained within a few hours where the solution concentration was about 1-2%,—within one day for a 2-3% concentration, up to two days for concentrations of about 5%, and up to three days for concentrations of 7-8%. A solution 22 was obtained that appeared clear until it was cooled in step 23 to a temperature of approximately 123° C., where it became opaque as the pseudo-gel was formed.

Figure 4:
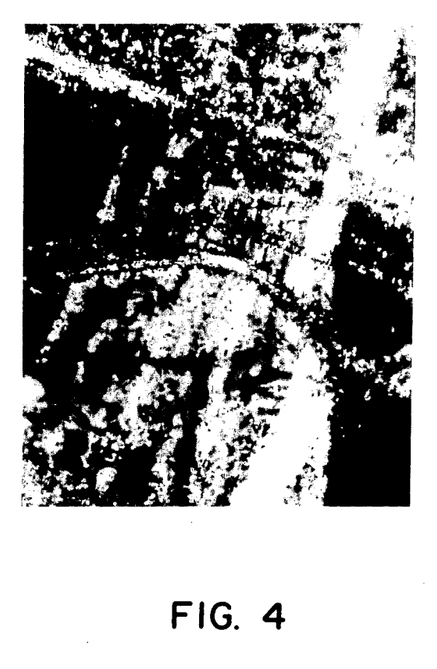
FIG. 4 is an optical photomicrograph at about 100× of a UHMWPE pseudo-gel morphology prepared under non-isothermal and quiescent conditions (NIQ). The morphology was viewed with cross-polarized light.

The uniformity of a so-produced UHMWPE pseudo-gel 24 depends on the conditions of preparation. When the crystals are grown in the concentrated solution under non-isothermal and quiescent conditions, herein called NIQ, the cooling rate is about 5° to 20° C. per minute without stirring, and the UHMWPE pseudo-gel is non-uniform and is comprised of a mixture of single crystals and a fibrillar network in which the fibrils have a shish-kebab crystalline morphology; the shish kebab fibrils in the UHMWPE pseudo-gel can be up to 2-3 mm. long and 20 μm. wide. This non-uniform structure is shown in FIG. 4.

Figure 5:
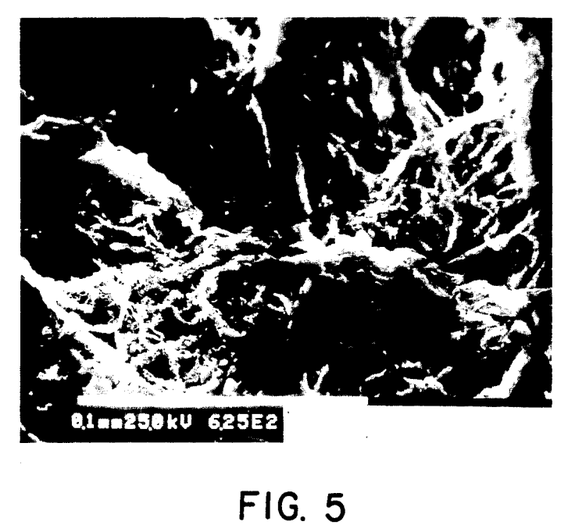
FIG. 5 is a reproduction of a scanning electron micrograph of a UHMWPE semicrystalline morphology obtained from the pseudo-gels after solvent extraction and drying, according to the invention, the pseudo-gel having been prepared under isothermal and non-quiescent conditions (INQ).
Figure 6:
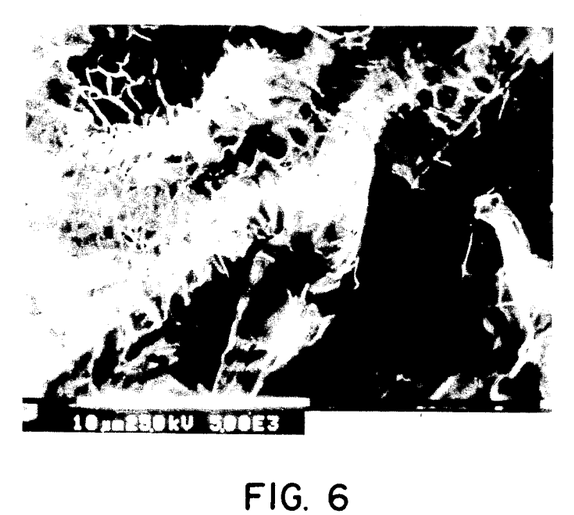
FIG. 6 is a similar scanning electron micrograph reproducion of a greater enlargement of the same kind of UHMWPE semicrystalline morphology of this invention the pseudo-gel having been prepared under isothermal and non-quiescent conditions (INQ).
Figure 7:
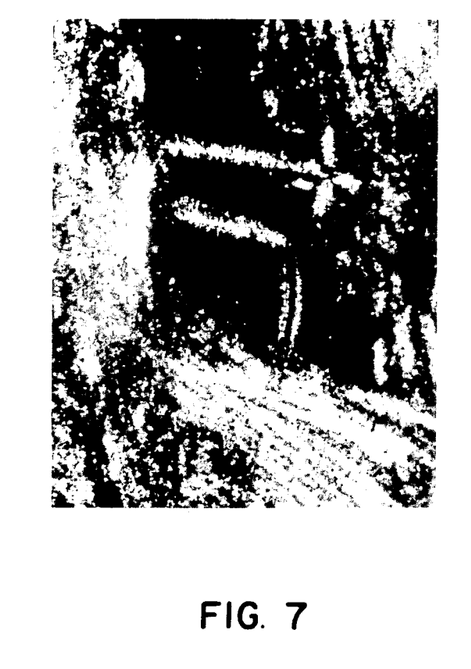
FIG. 7 is an optical photomicrograph at about 100× of a UHMWPE pseudo-gel morphology obtained under isothermal and non-quiescent conditions (INQ). The morphology was viewed with cross-polarized light.

The semicrystalline morphologies in FIGS. 5 and 6 were obtained from the pseudo-gel shown in FIG. 7 which was prepared under isothermal and non-quiescent conditions, herein called INQ. The solution was cooled to about 120° C., at a cooling rate of about 0.1° C. per minute, for three to five hours and was then kept at about 120° C. for one hour. During the entire cooling process, the solution was stirred. These semicrystalline morphologies were prepared by solvent extraction of the pseudo-gel followed by drying. FIG. 5 is a scanning electron micrograph of such a semicrystalline morphology; the degree of magnification is shown by the white bar which corresponds to 0.1 mm. in the actual semicrystalline morphology. A further magnification is shown in FIG. 6, when the white bar corresponds to 10 μm. FIG. 7 is taken from an optical photomicrograph of the pseudo-gel at about 100× and shows a typical shish-kebab fibrillar structure surrounded by randomly oriented single crystals and stacks of single crystals, as viewed with cross-polarized light.

Thus, UHMWPE pseudo-gels prepared under either non-isothermal or non-quiescent conditions exhibit remarkable continuity and resistance to shear deformation.

Figure 8:
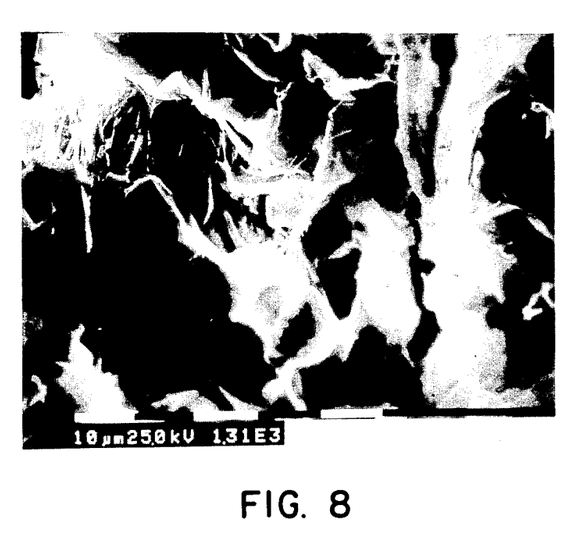
FIG. 8 is a similar scanning electron micrograph reproduction of a semicrystalline UHMWPE morphology of the invention obtained from the pseudo-gel after solvent extracting and drying, the pseudo-gel having been prepared under isothermal and quiescent conditions (IQ).
Figure 9:
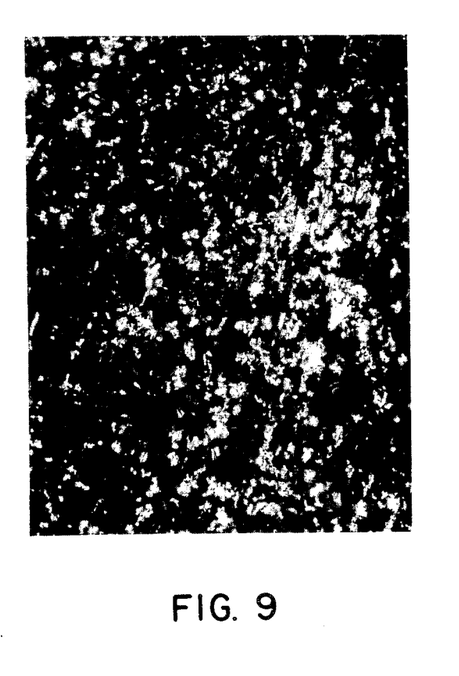
FIG. 9 is an optical photomicrograph at about 100× of a UHMWPE pseudo-gel morphology obtained under isothermal and quiescent conditions (IQ). The morphology was viewed with cross-polarized light.

The pseudo-gel shown in FIG. 9 was prepared under isothermal and quiescent conditions, herein called IQ. The same cooling process is used as for the INQ conditions, but without stirring during the cooling process. When the pseudo-gelation process occurs under isothermal and quiescent conditions, the pseudo-gel is more uniform, has a more turbid texture, and consists mainly of stacks of single crystals and large spherulitic crystals (up to 200 μm in diameter) with a significantly diminished fraction of shish kebab fibrils, and resistance to shear deformation. FIG. 8 is a scanning electron micrograph of the semicrystalline morphology obtained by solvent extraction and drying of a pseudo-gel like that of FIG. 9.

The different crystalline morphologies of the UHMWPE pseudo-gels obtained under different conditions of preparation can be ascertained also by the thermal behavior of the semicrystalline UHMWPE products which are obtained by extracting, in step 25, the paraffin oil from the pseudo-gel precursor with a more volatile solvent such as hexane, and subsequently evaporating out, step 26, the volatile solvent off in a drying process, leaving a semicrystalline UHMWPE morphology 27. The results of the thermal analysis are summarized in Table I.

TABLE I

Thermal analysis data of semicrystalline UHMWPE morphologies from gel-like precursors of different concentrations and different processing histories.

| Gel concentration (% W/W) | Tm (°C.) | Crystallinity (%) |
| --- | --- | --- |
| 2 | 137 | 72 |
| 3 | 136.5 | 76 |
| 4 | 136.4 | 72 |
| 5 | 137 | 75 |
| 5* | 129.8 | 73 |

*Pseudo-gel preparation under isothermal and quiescent conditions.

The first column of Table I indicates the percent concentration of the gel-like precursor, the second column the melting temperature of the semicrystalline morphologies after the evaporation of the volatile solvent, and the third column the percent crystallinity of these semicrystalline morphologies. The melting endotherms were obtained at 5° C./min. under $N_2$, and the degree of crystallinity was calculated, assuming that the heat of crystallization of a perfect polyethylene crystal is 293 J/g.

The thermal analysis results indicate that the melting temperature of the semicrystalline structures is independent of the concentration of the gel-like precursors which were obtained under non-isothermal non-quiescent conditions; however, it is lower when the gel-like precursor was prepared under isothermal and quiescent conditions. The higher melting endotherm of the crystalline structures at approximately 137° C. from pseudo-gels which were prepared under non-isothermal or non-quiescent conditions indicates that the crystals should have an extended chain configuration and is in agreement with the optical observations (e.g., FIG. 4) that so-produced pseudo-gels are comprised to a large extent of a shish kebab fibrillar network.

The lower melting endotherm of the crystalline structure at 129.9° C. from a gel-like precursor which was prepared under isothermal and quiescent conditions (see FIGS. 8 and 9) indicates that the crystals in this case have a chain-folded configuration, and, again, this is in agreement with the observation that the isothermally produced pseudo-gels under quiescent conditions are comprised of chain-folded crystals, like the stacks of single crystals and spherulites shown in FIGS. 8 and 9. Also, it is clear from the data in Table I that the percent crystallinity of the semicrystalline structure is independent of the studied concentration range of its gel-like precursors as well as its processing history.

A semicrystalline UHMWPE structure which is prepared from a pseudo-gel intermediate combines morphological features which cannot be exhibited by the morphologies obtained either by compacting the as-received fine powder stock or by melt crystallization. These morphological features arise from (a) the controlled material cohesion which is incomplete in the compacted powders and the melt-crystallized morphologies prepared by partial fusion, (b) the diminished, vis a vis the excessive, "amount of physical entanglements" in the melt-crystallized morphologies prepared by complete melting, and (c) the great variation of the crystalline morphology, from a chain-folded to an extended chain crystalline morphology, depending on the processing conditions during the preparation of the pseudo-gel precursor. The importance of the first two factors relates to the balanced enhancement of the deformability of the semicrystalline structures from gel-like precursors and their mechanical properties. The role of the third factor, and particularly the generation of a fibrillar network, comprised of extended-chain shish-kebab crystals, is important because such structure has a larger amount of free volume and consequently a high degree of porosity.

In comparison to the knitted and woven textures whose porosity can be adjusted to some extent by the thread size, interstices size, and the texturization of the synthetic fabric, the intrinsic fibrillar networks of this invention have the advantage that their porosity can be adjusted by thermal and mechanical means.

Thermal treatment may be brought about by heating the semicrystalline structure from a gel-like precursor to a temperature close to or above the melting point of the polymer and then cooling to ambient under modest compression (≦approximately 50 Atm). This treatment resulted in a significant porosity reduction.

Similarly, when a semicrystalline structure from a gel-like precursor was compressed at ambient temperature under 500 Atm, its porosity was reduced as a result of the densification process that takes place during the compression process.

The porosity of the semicrystalline structure from a gel-like precursor may be controlled also by the evaporation rate of the volatile solvent during the drying process as well as by solid-state deformation. The effects of pressure, temperature, and solid-state deformation on the percent porosity of UHMWPE semicrystalline morphologies from gel-like precursors of different concentrations are summarized in Table II.

TABLE II

The effect of temperature, pressure and solid state deformation on the percent porosity of UHMWPE semicrystalline morphologies from gel-like precursors of different concentrations.

| UHMWPE Sample | Porosity (%) |
| --- | --- |
| NIQ - pseudo-gel, 1% | 90.5 |
| NIQ - pseudo-gel, 2% | 51 |
| NIQ - pseudo-gel, 4% | 63 |
| SSD - pseudo-gel, 4%/DR = 4 | 49 |
| NIQ - pseudo-gel, 5% | 49 |
| SSD - pseudo-gel, 5%/DR = 8 | 40 |
| INQ - pseudo-gel, 5% | 78 |
| IQ - pseudo-gel, 5% | 79.5 |
| NIQ - pseudo-gel, 5%/compressed under 500 Atm | 0.2 |
| NIQ - pseudo-gel, 5%/heated to 140° C./50 Atm | 8.7 |
| NIQ - pseudo-gel, 8% | 49 |

TABLE II-continued

The effect of temperature, pressure and solid state deformation on the percent porosity of UHMWPE semicrystalline morphologies from gel-like precursors of different concentrations.

| UHMWPE Sample | Porosity (%) |
| --- | --- |
| melt crystallized | 7.3 |

NIQ = non-isothermal and quiescent conditions
INQ = isothermal and non-quiescent conditions
IQ = isothermal and quiescent conditions.
SSD = solid state deformed
DR = draw ratio The porosity was calculated from density determination, assuming that the density of polyethylene is 960 kgm$^{-3}$. The symbol NIQ indicates that the gel-like precursor was prepared under non-isothermal and quiescent conditions; INQ indicates that the gel-like precursor was prepared under isothermal and non-quiescent conditions; and IQ indicates that the gel-like precursor was prepared under isothermal and quiescent conditions. SSD indicates a semicrystalline morphology from an NIQ-pseudo-gel which was deformed in the solid state by tensile drawing at ambient temperature and at the indicated Draw Ratio (DR) determined by the cross-sectional areas before and after drawing.

The data in Table II indicates clearly that the porosity of the semicrystalline UHMWPE morphologies from gel-like precursors depends on the conditions of preparation and can be adjusted over a wide range from 0 to 90% by a suitable choice of temperature and pressure, and solid-state deformation.

Figure 2:
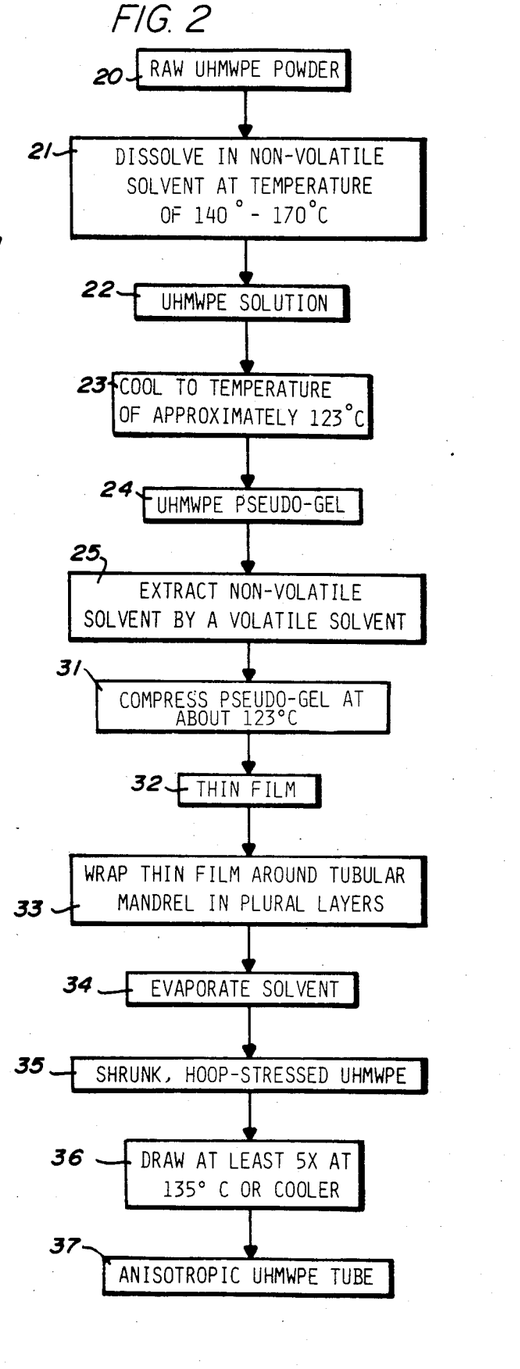
FIG. 2 is a flow sheet of another process embodying the principles of the invention.

As shown in FIG. 2, UHMWPE pseudo-gel states containing preferably a non-volatile solvent can be processed by molding or rolling under compression in step 31 to obtain thin gel-like film 32, preferably in a temperature range close to or above the temperature at which the pseudo-gel is formed (approximately 123° C.). Subsequently, the thin pseudo-gel film 32 can be wrapped in step 33 with or without tension on a mandrel to give a multilayer tubular structure, a proces which allows also for the build up of the tubular wall thickness. Cohesion of the successive pseudo-gel layers is achieved by a molecular reptation process which may occur between adjacent layers and result in a tubular wall with fraying resistance.

The volatile solvent such as n-hexane replaced the non-volatile solvent in step 25 and is removed by evaporation in step 34, to give a moderately shrunk, hoop stressed structure 35, in a drying step. Typically, the evaporation of the volatile solvent from the pseudo-gel is accompanied by considerable shrinkage, which when constrained has the advantage of resulting in the development of hoop stresses which enhance (a) the molecular chain orientation in the circumferential direction and consequently the lateral strength of the tubular structures and (b) the molecular chain interpenetration in the overlapping pseudo-gel layers, thus resulting in a coherent tubular wall.

Further enhancement of the mechanical performance of the tubular structures can be achieved by solid-state drawing in step 36 of the hoop-stressed dried tube 35. The process may result in tubular products 37 having a biaxially oriented fibrillar network structure with mechanical integrity along and across the draw direction. This integrity results from the superposition of the circumferential orientation, which is obtained by the constrained shrinkage during the evaporation of the volatile solvent, and the axial orientation during the solid-state deformation process on the mandrel. The solid-state deformation was performed at ambient temperature, and the draw ratio (DR) was calculated from the displacement of markers on the tubular wall after drawing.

Figure 10:
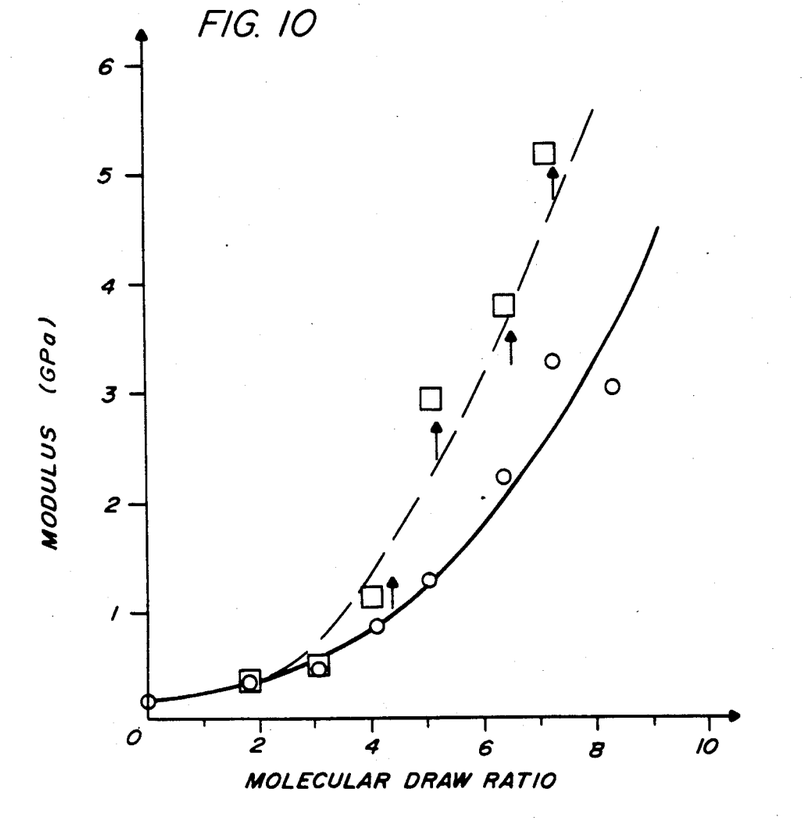
FIG. 10 is a graph plotting Young's modulus versus draw ratio for a UHMWPE of this invention. The solid-line curve represents observed values and the broken-line curve shows estimated maximum values for the UHMWPE of this invention.
Figure 11:
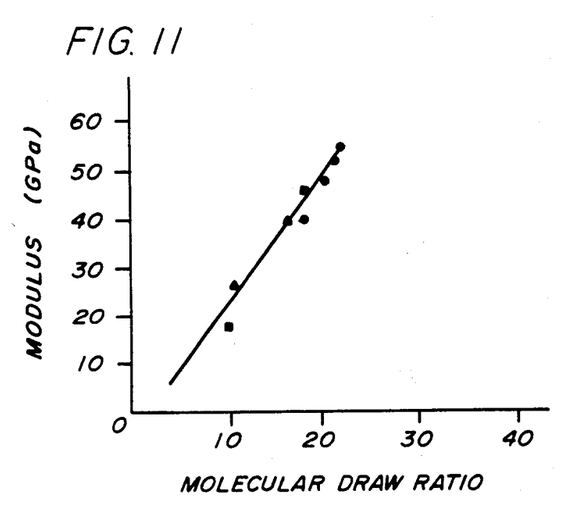
FIG. 11 is a similar graph for a conventional polyethylene, but not a UHMWPE.

FIG. 10 shows in a solid line curve average experimental modulus values at different draw ratios. The variation of experimentally determined initial modulus with the draw ratio is non-linear for the solid-state-drawn UHMWPE semicrystalline morphologies of this invention to a draw ratio of 8, in contrast to the previously established linear relation for melt-crystallized, high-density (not ultra-high molecular weight) polyethylene resins shown in FIG. 11; the difference is presumably due to the high porosity of the UHMWPE semicrystalline morphologies, in comparison to the low-porosity, melt-crystallized, high-density polyethylenes, which diminishes and allows for effective load transmission at significantly higher draw-ratios. FIG. 10 shows in a broken-line curve a graph of experimentally determined maximum initial modulus values from my new material at different draw ratios.

Figure 3:
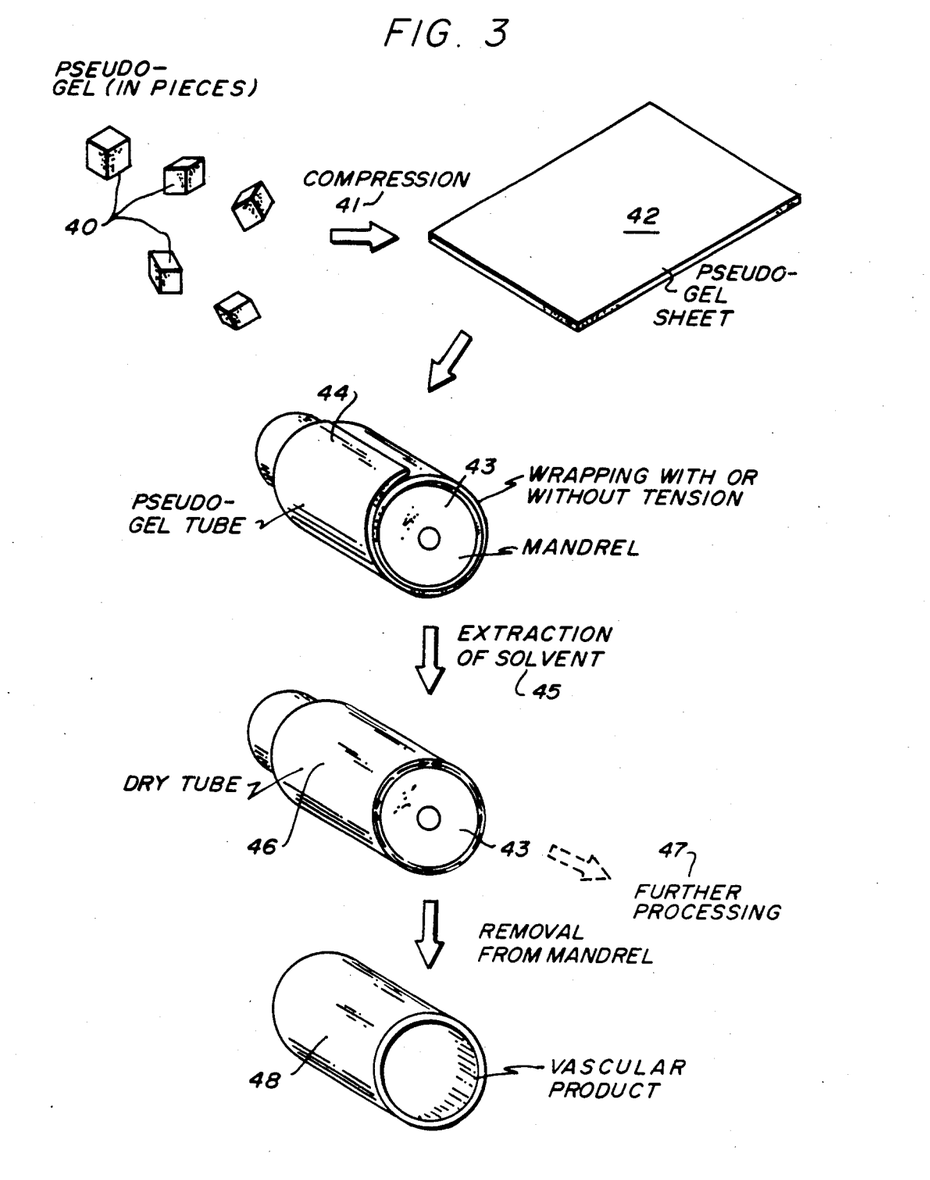
FIG. 3 is a flow sheet of a third process embodying the principles of the invention.

FIG. 3 shows a process much like that of FIG. 2. Pieces of pseudo-gel 40 are compressed at step 41 to make a gel-like sheet 42. The sheet 42 is wrapped around a mandrel 43 to produce a gel-like tube 44, which is then extracted at 45 to give a dry tube 46. This may be further processed, as at 47, as by drawing, or may be received from the mandrel 43 to give a vascular product 48.

Alternative methods for the preparation of tubular products with a biaxially oriented fibrillar network structure include processes such as solid-state extrusion through inverted conical dies and blowing air through the tubes. Both processes are also suitable for the preparation of biaxially oriented UHMWPE films which can be obtained by splitting the biaxially oriented tubes along their length. Also, some or most of the conventional thermoplastic processes, such as rolling, extrusion, drawing, compression molding, forging, and extrudo-rolling are amenable to processing UHMWPE semicrystalline morphologies from gel-like precursors into products with different profiles and geometric configurations and with adjustable mechanical properties over a wide range.

Tests in vivo indicate that artificial vascular prostheses made by this process can be handled conveniently and sutured to the natural vascular system readily. The vascular prostheses, isotropic UHMWPE semicrystalline tubes approximately 5-6 cm. long were implanted in the iliac aorta of mature dogs for an observation period of more than one year and exhibited very satisfactory anastomosis. Bleeding through the wall of the prosthesis was not observed during the implantation process. The prostheses are uniformly expansive under the pulsatile blood pressure and are flexible so that they bend without sharp corners. They do not show aneurysms at and beyond the anastomotic interfaces or along their body. (Aneurysms are local and progressive enlargements of vessel because of loss of vascular elasticity.)

The vascular prostheses of this invention can be fabricated in different geometric configurations, straight, crimped, smooth, or rough wall surfaces with adjustable porosities and mechanical properties over a wide range. Furthermore, this invention includes within its scope the use of isotropic and anisotropic UHMWPE morphologies from gel-like precursors in other biomedical application, such as orthopedic prostheses, sutures, and ligatures, in which a suitable combination of porosity and mechanical properties is necessary.

Other polymers which fall in the same category and can be obtained from gel-like precursors are ultra-high-molecular-weight polypropylene, polyvinyl alcohol, and other polymers capable of forming "pseudo-gel" states in suitable solvents such as polysaccharides, polyamides, polyesters and polyacrylonitrile. The amount of the polymer may be 1–20% in solvent of 99 to 80%, by weight. The melting point of the product will be within the range of 125°–270° C., depending on the particular product, as measured at a heating rate of about 5° C. per minute. The crystallinity may vary within the range of about 50% to about 75%.

To those skilled in the art to which this invention relates, many changes in construction and widely differing embodiments and applications of the invention will suggest themselves without departing from the spirit and scope of the invention. Such embodiments may include the fabrication of UHMWPE knitted and woven vascular prostheses, sutures, and composite structures of UHMWPE filamentary and non-filamentary semicrystalline morphologies. The disclosures and the descriptions herein are purely illustrative and are not intended to be in any sense limiting.

What is claimed is:

1. A tube of ultra-high-molecular-weight polyethylene semicrystalline morphology useful for vascular prostheses and having a Young's modulus of at least 3 GPa obtained by wrapping an ultra-high-molecular-weight polyethylene pseudo-gel on a mandrel, extracting the solvent with more volatile solvent and evaporating volatile solvent.

2. The tube of claim 1 in which the porosity is adjustable over the range of 0.2% to 90%.

3. A method for making an ultra-high-molecular-weight polyethylene product for use in vascular prostheses and the like, comprising,
    dissolving under slow-stirring conditions ultra-high-molecular-weight polyethylene in a solvent at an elevated temperature in the range of 140°–170° C.,
    cooling the solution at a rate less than 20° C. per minute to a temperature at which polymer crystals grow into an intercrystalline network that produces a pseudo-gel state, and
    extracting the solvent to produce a semicrystalline porous morphology.

4. The method of claim 3 wherein the cooling step is done under non-isothermal, quiescent conditions.

5. The method of claim 4 followed by drawing the semicrystalline morphology resulting from the extracting step, at a draw ratio of at least 5 and at a temperature in the range from ambient temperature to a temperature not exceeding the melting point of said semicrystalline morphology.

6. The method of claim 4, comprising, between the cooling and extracting steps, the step of compressing the gel.

7. The method of claim 3 wherein the cooling step is done under isothermal, non-quiescent conditions.

8. The method of claim 3 wherein the cooling step is done under isothermal, quiescent conditions.

9. A method of making an ultra-high-molecular-weight polyethylene product for use in vascular prostheses and the like, comprising,
    dissolving, under slow-stirring conditions of about 60–600 r.p.m., ultra-high-molecular-weight polyethylene in a non-volatile solvent at an elevated temperature in the range of 140°–170° C.,
    cooling the solution at a rate less than 20° C. per minute to a temperature in the vicinity of 120° to 125° C. at which polymer crystals grow into an intercrystalline network that produces a pseudo-gel state, and
    extracting the non-volatile solvent to produce a semicrystalline porous morphology.

10. The method of claim 9 wherein the cooling step is done under non-isothermal, quiescent conditions, at a cooling rate of about 5° to 20° C. per minute, without stirring.

11. The method of claim 10 followed by drawing the resulting product at a temerature no lower than ambient and no higher than the melting point of the semicrystalline porous morphology and at a draw ratio of at least 5.

12. The method of claim 10, comprising, between the cooling and extracting steps, compressing the gel between plates at 100° to 160° C.

13. The method of claim 9 wherein the cooling step is done under isothermal, non-quiescent conditions at a cooling rate of about 0.1° C. per minute, while stirring.

14. The method of claim 9 wherein the cooling step is done under isothermal, quiescent conditions at a cooling rate of about 0.1° C. per minute, without stirring.

15. A method for making a tubular profile of ultra-high-molecular-weight polyethylene with adjustable wall thickness, comprising the successive steps of
    wrapping an ultra-high-molecular-weight polyethylene pseudo-gel containing nonvolatile solvent on a mandrel,
    extracting the solvent from the pseudo-gel with a more volatile solvent, and
    evaporating the volatile solvent from the tubular profile.

16. The method of claim 15, comprising making an anisotropic ultra-high-molecular-weight polyethylene tubular structure by following the evaporating steps with the step of stretching the tube on the mandrel.

17. The method of claim 16 in which the temperature of stretching is from ambient temperature to the melting point of the semicrystalline porous morphology obtained after the evaporating step.

18. The method of claim 16 in which the draw ratio is at least 5×.

19. A method for making a tubular profile of ultra-high-molecular-weight polyethylene with adjustable wall thickness, comprising the steps of:
    dissolving said ultra-high-molecular-weight polyethylene in non-volatile solvent at an elevated temperature in the range of 140°–170° C.,
    cooling the solution at a rate of less than 20° C. per minute to a temperature at which polymer crystals grow into an intercrystalline network that provides a pseudo-gel,
    wrapping the gel around a mandrel,
    extracting the non-volatile solvent from the gel with a volatile solvent, and
    evaporating the volatile solvent from the tubular profile.

20. The method of claim 19 followed by stretching the tube on the mandrel at a temperature from ambient to 135° C. and at a draw ratio of at least 5×.

21. A method for making an ultra-high-molecular-weight polymer product for use in vascular prostheses and the like, comprising, slowly dissolving ultra-high-molecular-weight polymer in a solvent at an elevated temperature, cooling the solution at a rate below 20° C. per minute to a temperature at which polymer crystals grow into an intercrystalline network that produces a pseudo-gel state, and extracting the solvent to produce a semi-crystalline porous morphology.

22. The method of claim 21 wherein the cooling step is done under non-isothermal, quiescent conditions.

23. The method of claim 22 followed by drawing the semicrystalline morphology resulting from the extracting step, at a draw ratio of at least 5 and at a temperature in the range from ambient temperature to a temperature not exceeding the melting point of said semicrystalline morphology.

24. The method of claim 22, comprising, between the cooling and extracting steps, the step of compressing the gel.

25. The method of claim 21 wherein the cooling step is done under isothermal, non-quiescent conditions.

26. The method of claim 21 wherein the cooling step is done under isothermal, quiescent conditions.

27. A method for making a tubular profile of ultra-high-molecular-weight polymer with adjustable wall thickness, comprising the successive steps of wrapping an ultra-high-molecular-weight polymer pseudo-gel containing nonvolatile solvent on a mandrel, extracting the solvent from the pseudo-gel with a more volatile solvent, and evaporating the volatile solvent from the tubular profile.

28. The method of claim 27, comprising making an anisotropic ultra-high-molecular-weight polyethylene tubular structure by following the evaporating steps with the step of stretching the tube on the mandrel.

29. The method of claim 28 in which the temperature of stretching is from ambient temperature to the melting point of the semicrystalline porous morphology obtained after the evaporating step.

30. The method of claim 28 in which the draw ratio is at least 5×.

31. A method for making a tubular profile of ultra-high-molecular-weight polyethylene with adjustable wall thickness, comprising the steps of:

slowly dissolving said ultra-high-molecular-weight polyethylene in non-volatile solvent at an elevated temperature, in the range of 140°–170° C., cooling the solution at a rate lower than 20° C. per minute to temperature at which polymer crystals grow into an intercrystalline network that provides a pseudo-gel, wrapping the gel around a mandrel, extracting the non-volatile solvent from the gel with a volatile solvent, and evaporating the volatile solvent from the tubular profile.

32. A pseudo-gel comprising a suitable solvent in an amount of 99 to 90 percent by weight and an ultra-high-molecular-weight polyethylene in an amount of 1 to 10 percent by weight, said polyethylene being a semicrystalline network with adjustable crystalline morphology comprising randomly dispersed and oriented chain-folded single crystals, stacks of single crystals, spherulite crystals, and extended-chain shish-kebab-type of fibrils with lengths up to a few millimeters and widths up to 20 $\mu$m.

33. The semicrystalline ultra-high molecular-weight polyethylene obtained by removal of said solvent from the pseudo-gel of claim 32.

34. A semicrystalline morphology of ultra-high-molecular-weight polyethylene comprising randomly dispersed and oriented single crystals, stacks of single crystals, spherulitic crystals, and shish-kebab-type of fibrils with lengths up to a few millimeters and widths up to 20 $\mu$m, a melting point of 125°–140° C., measured at a heating rate of 5° C./min., a crystallinity of about 70%, measured on the basis that the heat of fusion of a perfect polyethylene crystal is 293 J/g., and a porosity from about 50 to 90%, measured on the basis that the density of polyethylene is 960 Kg/m$^3$.

35. A pseudo-gel comprising a suitable solvent in an amount of 99 to 80 percent by weight and an ultra-high-molecular-weight polymer in an amount of 1 to 20 percent by weight, said polymer being a semicrystalline network with adjustable crystalline morphology comprising randomly dispersed and oriented chain-folded single crystals, stacks of single crystals, spherulite crystals, and extended-chain shish-kebab-type of fibrils with lengths up to a few millimeters and widths up to 20 $\mu$m.

36. The semicrystalline ultra-high molecular-weight polymer obtained by removal of said solvent from the pseudo-gel of claim 35.

37. A semicrystalline morphology of ultra-high-molecular-weight polymer comprising randomly dispersed and oriented single crystals, stacks of single crystals, spherulitic crystals, and shish-kebab-type of fibrils with lengths up to a few millimeters and widths up to 20 $\mu$m., a melting point of 125°–270° C., depending on the particular polymer, measured at a heating rate of 5° C./min., a crystallinity of about 50% to about 75%.

* * * * *